United States Patent
Portillo Salido et al.

(10) Patent No.: US 8,569,271 B2
(45) Date of Patent: Oct. 29, 2013

(54) COMPOSITIONS COMPRISING TRAMADOL AND CELECOXIB IN THE TREATMENT OF PAIN

(75) Inventors: Enrique Portillo Salido, Barcelona (ES); Sebastia Videla Ces, Barcelona (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 13/394,995

(22) PCT Filed: Oct. 15, 2010

(86) PCT No.: PCT/EP2010/006317
§ 371 (c)(1),
(2), (4) Date: Mar. 8, 2012

(87) PCT Pub. No.: WO2011/045075
PCT Pub. Date: Apr. 21, 2011

(65) Prior Publication Data
US 2012/0172341 A1    Jul. 5, 2012

(30) Foreign Application Priority Data
Oct. 16, 2009 (EP) .................................... 09384004

(51) Int. Cl.
*A61K 31/63* (2006.01)
*A61K 31/13* (2006.01)
(52) U.S. Cl.
USPC .......................................... 514/158; 514/659
(58) Field of Classification Search
None
See application file for complete search history.

(56) References Cited

U.S. PATENT DOCUMENTS

| 5,516,803 A | 5/1996 | Raffa |
| 6,558,701 B2 | 5/2003 | Bartholomaeus et al. |
| 2005/0090517 A1 | 4/2005 | Norris |
| 2008/0031950 A1 | 2/2008 | Sesha |

FOREIGN PATENT DOCUMENTS

| EP | 0 546 676 | 6/1993 |
| WO | 00/51685 | 9/2000 |
| WO | 0051685 A | 9/2000 |

OTHER PUBLICATIONS

Goldenberg MM. Celecoxib, a selective cyclooxygenase-2 inhibitor for the treatment of rheumatoid arthritis and osteoarthritis. Clin. Ther. 1999, 21, 1497-513.
International Search Report for PCT/EP2010/006317 dated Dec. 20, 2010.
Chandran P et al: "Pharmacological modulation of movement-evoked pain in a rat model of osteoarthritis," European Journal of Pharmacology, Elsevier, BV, NL, Jun. 24, 2009, pp. 39-45, vol. 613, No. 1-3.
Hersh et al: "Adverse drug interactions involving common prescription and over-the-counter analgesic agents," Clinical Therapeutics, Excerpta Medica, Jan. 1, 2007, pp. 2477-2497, vol. 29, No. 11, Princeton, New Jersey.
Graham R Evans et al: "Development of Highly Efficient Resolutions of Racemic Tramadol Using Mandelic Acid," Organic Process Research and Development, Jan. 1, 2002, pp. 729-737, vol. 6, Cambridge, Great Britain.

*Primary Examiner* — Sreeni Padmanabhan
*Assistant Examiner* — Jody Karol
(74) *Attorney, Agent, or Firm* — Heslin Rothenberg Farley & Mesiti P.C.

(57) ABSTRACT

The present invention relates to pharmaceutical compositions comprising tramadol and celecoxib and their uses as medicaments or analgesics, more particularly for the treatment of severe to moderate pain with an inflammation component.

4 Claims, 1 Drawing Sheet

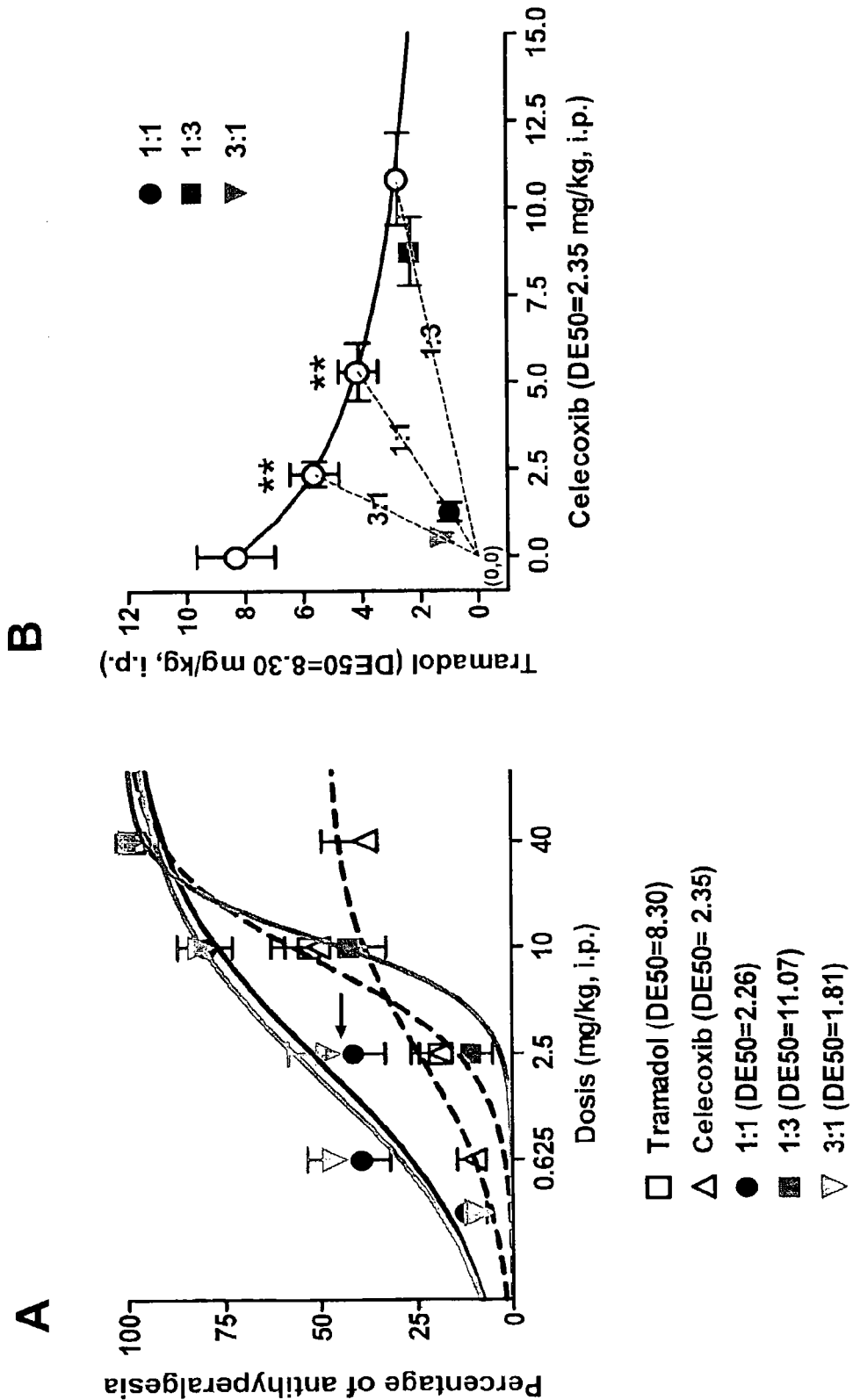

COMPOSITIONS COMPRISING TRAMADOL AND CELECOXIB IN THE TREATMENT OF PAIN

CROSS REFERENCE TO RELATED APPLICATIONS

This application is a U.S. National Phase filing under 35 U.S.C. §371 of International Application PCT/EP2010/006317, filed Oct. 15, 2010, and published as WO 2011/045075 on Apr. 21, 2011. PCT/EP2010/006317 claimed benefit of priority from European Patent Application No. EP 09384004.9, filed Oct. 16, 2009. The entire contents of each of the prior applications are incorporated herein by reference.

The present invention relates to pharmaceutical compositions comprising tramadol and celecoxib and their uses as medicaments or analgesics, more particularly for the treatment of severe to moderate pain.

Pain is a complex response that has been functionally categorized into sensory, autonomic, motor, and affective components. The sensory aspect includes information about stimulus location and intensity while the adaptive component may be considered to be the activation of endogenous pain modulation and motor planning for escape responses. The affective component appears to include evaluation of pain unpleasantness and stimulus threat as well as negative emotions triggered by memory and context of the painful stimulus.

In general, pain conditions can be divided into chronic and acute. Chronic pain includes neuropathic pain and chronic inflammatory pain, for example arthritis, or pain of unknown origin, as fibromyalgia. Acute pain usually follows non-neural tissue injury, for example tissue damage from surgery or inflammation, or migraine. Pain may also be divided into different levels of severity starting from severe through moderate to light pain.

There are many drugs that are known to be useful in the treatment or management of pain. Opioids are frequently used as analgesics in pain. Derivatives of morphine are indicated for the treatment of moderate to acute pain in human. The analgesic effect is obtained through their action on morphinic receptors, preferably the μ-receptors. Among these derivatives of morphine, morphine, codeine, pethidine, dextropropoxyphenemethadone, lenefopan may be mentioned.

One of the morphinic derivatives that has shown very good results when orally administrated, and which is extensively marketed, is tramadol, also available as a physiologically acceptable salt, particularly as a chlorohydrate. Tramadol is a central acting analgesic drug that exerts its effects by activating opioid receptors and enhancing neuronal monoamine synaptic concentration. Tramadol, whose chemical name is 2-(dimethylaminomethyl)-1-(3-methoxyphenyl)cyclohexanol, has the following formula:

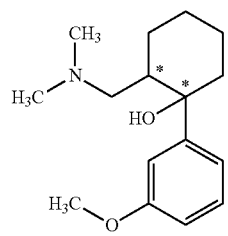

Tramadol

This structure shows two different chiral centers and thus the molecule may exist in different diastereoisomers among which the tramadol is the cis-diastereoisomer. The enantiomers (1R,2R), or (1S,2S), are also known as (+)-tramadol and (−)-tramadol with both of them contributing in different ways to the overall activity of racemic tramadol.

"(rac)" is according to this invention defined as the abbreviation of "racemate" and thus "(rac)-tramadol" or "(rac) tramadol" means racemic tramadol (the cis-diastereoisomer) as described in the paragraph above.

Accordingly, "(rac)-tramadol·HCl" or "(rac) tramadol·HCl" is defined as the hydrochloride salt of racemic tramadol (the cis-diastereoisomer) as described above.

From the art it appears that this compound is neither fully opioid-like, nor non-opioid-like. Some studies have demonstrate that tramadol is an opioid agonist, whereas clinical experience indicates that it lacks many of the typical side effects of opioids agonist, for example respiratory depression, constipation or tolerance.

Due to their drawbacks, opioids used as analgesics to treat pain cannot always be given repeatedly or at higher doses. The effects of opioids are reviewed for example by J. Jaffe in "Goodman and Gilman's, The Pharmacological Basis of Therapeutics", 8th edition; Gilman et al.; Pergamon Press, New York, 1990, Chapter 22, pages 522-573.

Consequently it has been proposed to combine opioids with other drugs that are not opioid analgesic agents, in order to lower the amount of opioids needed to produce an equivalent degree of analgesia. Among these combinations, the association of tramadol with nonsteroidal anti-inflammatory drugs (NSAIDs) has been reported to be of particular interest (EP-0 546 676).

U.S. Pat. No. 5,516,803 discloses combination of tramadol with non-steroidal anti-inflammatory drugs (NSAIDs), specifically ibuprofen and discloses the combination of tramadol·HCl with non-steroidal anti-inflammatories, such as for example ibuprofen, in a composition ratio of 1:1 to 1:200 producing a synergistically enhanced analgesic action and reducing the undesired accompanying symptoms U.S. Pat. No. 6,558,701 patent discloses combination of tramadol with diclofenac and "for the treatment of moderate to severe pain, the World Health Organization (WHO) recommends combining opioid analgesics with non-steroidal analgesics in order to produce a more effective pain relief and possibly reduce amounts of analgesic which are necessary to administer".

One interesting NSAIDs to be combined with tramadol is the marketed drug celecoxib, whose chemical name is 4-[5-(4-methylphenyl)-3-(trifluoromethyl)-pyrazol-1-yl]-benzenesulfonamide. Celecoxib is an anti-inflammatory and pain killer drug and it is one of the most used treatments for chronic musculo-skeletal inflammatory illnesses. It has an empirical formula of $C_{17}H_{14}F_3N_3O_2S$.

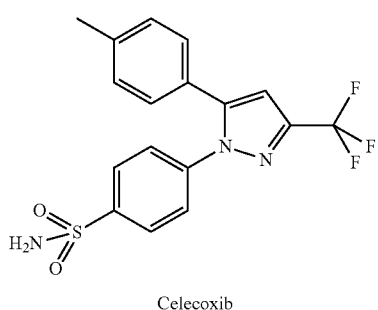 [SMILES: Cc1ccc(-c2cc(C(F)(F)F)nn2-c2ccc(S(N)(=O)=O)cc2)cc1]

Celecoxib

Celecoxib is an oral, highly selective cyclooxygenase-2 (COX-2) inhibitor, and it is indicated for the treatment of symptomatic relief in the treatment of osteoarthritis, rheumatoid arthritis and ankylosing spondylitis (Goldenberg MM. Celecoxib, a selective cyclooxygenase-2 inhibitor for the treatment of rheumatoid arthritis and osteoarthritis. *Clin. Ther.* 1999, 21, 1497-513). This high selectivity allows celecoxib and other COX-2 inhibitors to reduce inflammation (and pain) while minimizing gastrointestinal adverse drug reactions (e.g. stomach ulcers) that are common with non-selective NSAIDs.

Cyclooxygenase is responsible for generation of prostaglandins. Two isoforms, COX-1 and COX-2, have been identified. COX-2 is the isoform of the enzyme that has been shown to be induced by pro-inflammatory stimuli and has been postulated to be primarily responsible for the synthesis of prostanoid mediators of pain, inflammation, and fever. COX-2 is also involved in ovulation, implantation and closure of the ductus arteriosus, regulation of renal function, and central nervous system functions (fever induction, pain perception and cognitive function). It may also play a role in ulcer healing. COX-2 has been identified in tissue around gastric ulcers in man but its relevance to ulcer healing has not been established.

WO00/51685 describes pharmaceutical composition comprising on one hand a tramadol material selected from:
 (+)- and (−)-tramadol, racemic tramadol, the N-oxide of tramadol and O-desmethyl-tramadol (both of them as isolated stereoisomers or mixtures thereof including their racemates) either as free base or as a salt, solvate or polymorph;
and on the other hand a selective COX-2 inhibitor with celecoxib being listed among the COX-2 inhibitor drugs. The focus of the application rests in the exemplified combination of tramadol and JT-522.

The applicant has now found that tramadol, especially the (rac)-tramadol hydrochloride salt, having the opioid activity, and celecoxib (especially in its neutral form) can be combined in one pharmaceutical composition achieving an additive effect, especially in the treatment of severe to moderate pain, especially in pain with an inflammatory element.

Thus the object of the present invention is a pharmaceutical composition comprising a combination of (rac)tramadol·HCl and celecoxib or a pharmaceutically acceptable salt or hydrate thereof.

In general each separate active principle of the pharmaceutical composition according to the invention, the tramadol and the celecoxib, has its own disadvantages when used alone.

Thus, tramadol hydrochloride, which is often used orally, displays a highly bitter taste, which makes the drugs often difficult to swallow and lowers patient compliance. Also, as stated before, the drawbacks associated with opioids—their side effects—are limiting their use, so that they have to be given at lower doses and often less frequent as their use as analgesics to treat pain would normally require. On the other hand celecoxib is well-known to be only slightly soluble in water and this is further limiting its use in pharmaceutical formulations.

The object of the present invention is to provide a pharmaceutical composition comprising an opioid like tramadol and an NSAID like celecoxib having a level of efficacy similar to the one achievable by each active substance used alone, but:
 with a better safety profile at higher doses and/or
  —by showing a synergistic effect—allowing a reduction of dose while still delivering the desired activity using less of each ingredient and, therefore, reducing the side effects associated with each active principle; and/or
 providing a new more effective method for treating acute or severe to moderate pain, especially in pain with an inflammatory component.

Other desirable improvements/advantages of the new pharmaceutical composition would include being active in diseases or symptoms being or related to pain and its subtypes, especially those in which current treatment is insufficient like sciatica or frozen shoulder or pain related to central sensitization (central pain syndrome).

Most desirably the pharmaceutical composition should combine more than one, most preferably all of these advantages.

This pharmaceutical composition according to the invention shows improved properties if compared to any of the active principles alone.

In one preferred embodiment of the pharmaceutical composition according to the invention the celecoxib is in neutral form.

As celecoxib is weakly acidic with a pKa of 11.1 its "neutral form" according to the invention is defined therefore as the form in which celecoxib is free (not in form of a salt) but is—depending on the pH—neutral or carrying a load.

In one further embodiment of the pharmaceutical composition according to the invention the ratio of the (rac)-tramadol·HCl to the celecoxib is a weight ratio of from about 1:1 to about 1:300 or from about 1:1 to about 300:1.

In one further embodiment of the pharmaceutical composition according to the invention the ratio of the (rac)-tramadol·HCl to the celecoxib is a molar ratio of from about 1:1 to about 1:300 or from about 1:1 to about 300:1.

In one further embodiment of the pharmaceutical composition according to the invention the molecular ratio of the (rac)-tramadol·HCl to the celecoxib is a weight ratio of from about 1:1 to about 1:30 or from about 1:1 to about 30:1.

In one further embodiment of the pharmaceutical composition according to the invention the molecular ratio of the (rac)-tramadol·HCl to the celecoxib is a molar ratio of from about 1:1 to about 1:30 or from about 1:1 to about 30:1.

In one further embodiment of the pharmaceutical composition according to the invention the molecular ratio of the (rac)-tramadol·HCl to the celecoxib is a molar ratio of from about 1:1 to about 1:5 or from about 1:1 to about 5:1.

Another advantage is that the association of the two active principles into one unique species seems to allow for a better Pharmacokinetic/Pharmacodynamic (PKPD) including also a better penetration of the blood-brain barrier, which helps in the treatment of pain.

Both parts of the pharmaceutical composition are well-known drugs used for a long time worldwide. Due to the therapeutic interest in tramadol in the treatment of pain symptoms and the well-known properties of celecoxib in this field of medical indication, a further object of the present invention is a medicament containing a pharmaceutical composition comprising (rac)-tramadol.HCl and celecoxib.

Thus, the invention also relates to a medicament containing a pharmaceutical composition comprising (rac)-tramadol.HCl and celecoxib according to the invention as described above and optionally one or more pharmaceutically acceptable excipients.

The medicament or pharmaceutical composition according to the present invention may be in any form suitable for the application to humans and/or animals, preferably humans including infants, children and adults and can be produced by standard procedures known to those skilled in the art. The medicament can be produced by standard procedures known to those skilled in the art, e.g. from the table of contents of "Pharmaceutics: The Science of Dosage Forms", Second Edition, Aulton, M. E. (ED. Churchill Livingstone, Edinburgh (2002); "Encyclopedia of Pharmaceutical Technology", Second Edition, Swarbrick, J. and Boylan J. C. (Eds.), Marcel Dekker, Inc. New York (2002); "Modern Pharmaceutics", Fourth Edition, Banker G. S. and Rhodes C. T. (Eds.) Marcel Dekker, Inc. New York 2002 y "The Theory and Practice of Industrial Pharmacy", Lachman L., Lieberman H. And Kanig J. (Eds.), Lea & Febiger, Philadelphia (1986). The respective descriptions are hereby incorporated by reference and form part of the disclosure. The composition of the medicament may vary depending on the route of administration.

The medicament or pharmaceutical composition of the present invention may for example be administered parentally in combination with conventional injectable liquid carriers, such as water or suitable alcohols. Conventional pharmaceutical excipients for injection, such as stabilizing agents, solubilizing agents, and buffers, may be included in such injectable compositions. These medicaments or pharmaceutical compositions may for example be injected intramuscularly, intraperitoneally, or intravenously.

Medicaments or pharmaceutical compositions according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, granules, capsules, lozenges, aqueous or oily solutions, suspensions, emulsions, or dry powdered forms suitable for reconstitution with water or other suitable liquid medium before use, for immediate or controlled release. The multiparticulate forms, such as pellets or granules, may e.g. be filled into a capsule, compressed into tablets or suspended in a suitable liquid.

Suitable controlled release formulations, materials and methods for their preparation are known from the prior art, e.g. from the table of contents of "Modified-Release Drug Delivery Technology", Rathbone, M. J. Hadgraft, J. and Roberts, M. S. (Eds.), Marcel Dekker, Inc., New York (2002); "Handbook of Pharmaceutical Controlled Release Technology", Wise, D. L. (Ed.), Marcel Dekker, Inc. New York, (2000); "Controlled Drug Delivery", Vol, I, Basic Concepts, Bruck, S. D. (Ed.), CRD Press Inc., Boca Raton (1983) y de Takada, K. and Yoshikawa, H., "Oral Drug Delivery", Encyclopedia of Controlled Drug Delivery, Mathiowitz, E. (Ed.), John Wiley & Sons, Inc., New York (1999), Vol. 2, 728-742; Fix, J., "Oral drug delivery, small intestine and colon", Encyclopedia of Controlled Drug Delivery, Mathiowitz, E. (Ed.), John Wiley & Sons, Inc., New York (1999), Vol. 2, 698-728. The respective descriptions are hereby incorporated by reference and form part of the disclosure.

Medicaments or pharmaceutical compositions according to the present invention may also comprise an enteric coating, so that their dissolution is dependent on pH-value. Due to said coating the medicament may pass the stomach undissolved and the respective pharmaceutical composition and its components is/are liberated in the intestinal tract. Preferably the enteric coating is soluble at a pH value of 5 to 7.5. Suitable materials and methods for the preparation are known from the prior art.

Typically, the medicaments or pharmaceutical compositions according to the present invention may contain 1-60% by weight of the combination of (rac)-tramadol.HCl and celecoxib as defined herein and 40-99% by weight of one or more auxiliary substances (additives/excipients).

The compositions of the present invention may also be administered topically or via a suppository.

The daily dosage for humans and animals may vary depending on factors that have their basis in the respective species or other factors, such as age, sex, weight or degree of illness and so forth. The daily dosage for humans preferably is in the range of 10 to 2000 milligrams of active substance to be administered during one or several intakes per day.

A further aspect of the invention relates to a pharmaceutical composition according to the invention comprising the combination of (rac)-tramadol.HCl and celecoxib according to the invention for use as an analgesic for the treatment of pain, preferably acute pain, chronic pain, neuropathic pain, hyperalgesia, allodynia or cancer pain, including diabetic neuropathy and osteoarthritis; as well as severe to moderate pain; including also rheumatoid arthritis, ankylosing spondylitis, sciatica and frozen shoulder. The use of the pharmaceutical composition might especially be drawn to the treatment of severe to moderate pain with an inflammatory component like e.g. rheumatoid arthritis, ankylosing spondylitis, sciatica and frozen shoulder.

A further aspect of the invention relates to a pharmaceutical composition according to the invention comprising the combination of (rac)-tramadol.HCl and celecoxib according to the invention for use as an analgesic or for the treatment of pain, preferably acute pain, chronic pain (acute and chronic pain), neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica. A further aspect of the invention relates to a pharmaceutical composition according to the invention comprising the combination of (rac)-tramadol.HCl and celecoxib according to the invention for the treatment of pain, preferably acute pain, or preferably acute pain, chronic pain (acute and chronic pain), neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica. The invention thus also relates to the use of a co-crystal according to the invention as described above in the production of a medicament for the treatment of pain, preferably acute pain, chronic pain (acute and chronic pain), neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica.

A related further aspect of the invention is aimed at the use of a pharmaceutical composition according to the invention as described above in the manufacture of a medicament for the treatment of pain, preferably acute pain, chronic pain, neuropathic pain, hyperalgesia, allodynia or cancer pain, including diabetic neuropathy, fibromyalgia or osteoarthritis; as well as severe to moderate pain; including also rheumatoid arthritis, ankylosing spondylitis, sciatica and frozen shoulder. Preferably this use is provided for in form of a medicament or a pharmaceutical composition according to the invention as described above. This medicament might especially be drawn to the treatment of severe to moderate pain with an inflammatory component like e.g. rheumatoid arthritis, ankylosing spondylitis, sciatica and frozen shoulder. Another related further aspect of the invention is aimed at the use of a pharmaceutical composition according to the invention as described above in the manufacture of a medicament for the treatment of pain, preferably acute pain, chronic pain (acute and chronic pain), neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica.

Another object of the current invention is a method of treatment of pain, preferably acute pain, chronic pain, neuropathic pain, hyperalgesia, allodynia or cancer pain, including diabetic neuropathy, fibromyalgia or osteoarthritis; as well as severe to moderate pain; including also rheumatoid arthritis, ankylosing spondylitis, sciatica and frozen shoulder, by providing to a patient in need thereof a sufficient amount of the pharmaceutical composition comprising the combination of (rac)-tramadol.HCl and celecoxib according to the invention as described above. This method of treatment might especially be relevant for the treatment of severe to moderate pain with an inflammatory component like e.g. rheumatoid arthritis, ankylosing spondylitis, sciatica and frozen shoulder. Another related object of the invention is aimed at a method of treatment of pain, preferably acute pain, chronic pain (acute and chronic pain), neuropathic pain, nociceptive pain (visceral and/or somatic pain), mild and severe to moderate pain, hyperalgesia, pain related to central sensitization, allodynia or cancer pain, including diabetic neuropathy or diabetic peripheral neuropathy and osteoarthritis, fibromyalgia; rheumatoid arthritis, ankylosing spondylitis, frozen shoulder or sciatica by providing to a patient in need thereof a sufficient amount of the pharmaceutical composition comprising the combination of (rac)-tramadol.HCl and celecoxib according to the invention as described above.

"Pain" is defined by the International Association for the Study of Pain (IASP) as "an unpleasant sensory and emotional experience associated with actual or potential tissue damage, or described in terms of such damage (IASP, Classification of chronic pain, $2^{nd}$ Edition, IASP Press (2002), 210). Even though pain is always subjective its causes or syndromes can be classified. One classification to denominate subtypes of pain would be to divide the general pain syndrome into the subtypes of acute and chronic pain or—according to the pain intensity—into mild, moderate and severe pain. In other definitions the general pain syndrome is also divided into "nociceptive" (caused by activation of nociceptors), "neuropathic" (caused by damage to or malfunction of the nervous system) and pain related to central sensitization (central pain syndrome).

"Sciatica" or "sciatic neuritis" is defined herein as a set of symptoms including pain that derive from irritation of the sciatic nerve or its roots, "Frozen shoulder" or "adhesive capsulitis" is defined herein as a symptom wherein the connective tissue surrounding the shoulder joint or the shoulder capsule itself is causing chronic pain, becoming inflamed and stiff.

"Ankylosing spondylitis" or "Morbus Bechterew" is a chronic, inflammatory arthritis and autoimmune disease. It mainly affects joints in the spine and the sacroilium in the pelvis, causing eventual fusion of the spine.

"Pain related to central sensitization"/"central pain syndrome" is defined within this application as a neurological condition caused by damage to or dysfunction of the central nervous system (CNS), which includes the brain, brainstem, and spinal cord. This syndrome can inter alia be caused by stroke, multiple sclerosis, tumors, epilepsy, brain or spinal cord trauma, or Parkinson's disease.

"Nociceptive pain" is defined as a type of pain caused by activation of nociceptors. It can be divided into somatic and visceral pain. "Visceral pain" is pain generally originating from the organs, whereas "(deep) somatic pain" originates from ligaments, tendons, bones, blood vessels, fasciae and muscles.

BRIEF DESCRIPTION OF THE FIGURES

FIG. 1:

A: Dose response curves of antihyperalgesic effects of tramadol, celecoxib and different combinations of racemic tramadol hydrochloride with celecoxib at different ratios (1:1, 1:3 and 3:1) in the rat paw incision model of postoperative pain.

B: Isobologram analysis showing significant ($p<0.01$) synergistic interaction on thermal hyperalgesia. All data are presented as means±SEM (n=10-13 per dose group).

The present invention is illustrated below with the help of the following examples. These illustrations are given solely by way of example and do not limit the invention.

EXAMPLES

Example 1

Preparation of Composition Doses of Tramadol Hydrochloride and Celecoxib

Combinations of a racemic tramadol hydrochloride and celecoxib were prepared at different molar ratios of (rac)-tramadol.HCl:celecoxib (1:1, 1:3 and 3:1). All drugs and combinations were dissolved in 0.5% hydroxypropyl methylcellulose in distilled water and administered in a volume of 10 ml/kg per rat through the intraperitoneal (i.p.) route. In Table 1 are listed the different ratios prepared at the various concentrations,

TABLE 1

Corresponding doses of each drug or combinations administered intraperitoneally.

| | Doses (mg/kg) | | | | |
|---|---|---|---|---|---|
| Tramadol | 2.5 | 10 | 40 | | |
| Celecoxib | 0.625 | 2.5 | 10 | 40 | |
| Ratio 1:1 | 0.3130 | 0.625 | 2.5 | 10 | 40 |
| Ratio 1:3 | 2.5 | 10 | 40 | | |
| Ratio 3:1 | 0.625 | 2.5 | 10 | 40 | |

Effects on Thermal Hyperalgesia in a Postoperative Pain Model in Rat

The aim of this study was to evaluate the analgesic efficacy and potency of compositions comprising a combination of tramadol/celecoxib, especially a combination of racemic tramadol hydrochloride with celecoxib in different molar ratios (1:1, 1:3 and 3:1) in a rat model of postoperative pain after paw incision. To assess the reliability of the efficacy and potency of the compounds tested thermal hypersensitivity (hyperalgesia) was performed using the plantar test assay (Hargreaves et al., Pain 1988, 32, 77).

Experimental Design:

Animals

Male, Wistar rats (120-160 g, Harlan, Italy) were housed in a climate-controlled room for at least 5 days prior to testing. Food and water were available ad libitum up to test time.

Animal Dosing

The rats were all dosed intraperitoneally with compositions comprising a combination of racemic tramadol hydrochloride and celecoxib at different ratios, dissolved in a suspension of 0.5% hydroxypropyl methylcellulose in distilled water. The dosing volume was 10 ml/kg. The antihyperalgesic response of the animal was subsequently evaluated 60 min after compositions administration.

Surgery

Rats were anaesthetized with 3% isofluorane and a 1 cm longitudinal incision was made through skin and fascia of the plantar surface of the paw, starting 0.5 cm from the proximal edge of the heel and extending toward the toes. Both superficial (skin) and deep (muscle) tissues and nerves were injured. Finally, the skin of the paw was stitched with a suturing stitch with breaded silk (3.0).

Assessment of Analgesic Activity in Post-Operative Pain in Rats

The drugs were tested 4 hours after the surgery (plantar incision); 60 minutes after the administration of the product, Assessment of Thermal Hypersensitivity (Hyperalgesia) in Post-Operative Pain in Rats Thermal hypersensitivity or hyperalgesia was assessed by measurement of a response to a thermal stimulus using a Hargreaves apparatus (Ugo Basile plantar test) which selectively elevates the temperature of an individual paw (Ding, et al., J Neurosci Methods, 1997, 76, 183). Animals were placed in the methacrylate cages of said apparatus, having a crystal floor. The acclimation period within the cages was about 10 minutes. The thermal stimulus came from a lamp moving below the crystal floor and which was applied to both paws, with a minimum interval of 1 minute between both stimulations in order to avoid learning behaviours. The rat is able to withdraw the paw freely when it feels discomfort (pain) produced by the heat coming from the lamp; then it is switched off and the latency time to the withdrawal response is recorded in seconds. In order to avoid hurting the animal's paw, the lamp was automatically switched off after 32 seconds. Hyperalgesia is defined as an increased response to a painful stimulus and the analgesic effect of the test compound is seen as a (partial) restoration of the latency toward normal (Dirig, et al., J. Pharmacol Expt Therap. 1998, 285, 1031).

Analysis of Synergistic Effect

The synergistic interaction between tramadol and celecoxib was determined by isobologram analysis as discloses by R. J. Tallarida, et al., Life Sci., 1989, 45, 947. This procedure involves the determination of the total amount in the mixture that is required to produce a specified synergistic anti-hyperalgesic effect at the 50% dose level (that is, the $ED_{50}$ or Zt) and the corresponding total amount that would be expected under simple additivity ($ED_{50}$ add or Zadd). Where it is established that Zt<Zadd for a specific fixed-ratio, then that composition has a synergistic anti-hyperalgesic effect. Both $ED_{50}$ t and $ED_{50}$ add values are random variables. $ED_{50}$ t is determined from the dose-response curve for a specific fixed-ratio of the components; $ED_{50}$ add is calculated from the $ED_{50}$ values for the individual drugs. Zt is then compared to Zadd via a Student's t-test.

Results:

In this study, dose response curves of compositions comprising a combination of racemic tramadol hydrochloride and celecoxib at different ratios (1:1, 1:3 and 3:1) were obtained (see FIG. 1A). All drugs induced full efficacy when thermal hypersensitivity was evaluated.

All ratios of combination of racemic tramadol hydrochloride with celecoxib resulted to act synergistically inhibiting thermal hyperalgesia in postoperative pain rats. The ratios 1:1 and 3:1 improved significantly around 4 times the antihyperalgesic effects. The ratio 1:3 improved around 1 time the antihyperalgesic effects (see Table 2 and FIG. 1B).

TABLE 2

Statistic comparative analysis of Zt (experimental) versus Zadd (additive) using a student's t-test.

| Combination ratio | Zt | Zadd | Ratio |
| --- | --- | --- | --- |
| 1:1 | 2.26 ± 0.48** | 9.41 ± 1.49 | 4.16 |
| 3:1 | 1.81 ± 0.41** | 7.97 ± 1.2 | 4.40 |
| 1:3 | 11.07 ± 1.25 | 13.59 ± 1.67 | 1.23 |

CONCLUSION

Compositions comprising a combination of racemic tramadol hydrochloride and celecoxib show synergistic interaction to inhibit thermal hyperalgesia in the rat paw incision postoperative pain model.

The invention claimed is:

1. A pharmaceutical composition comprising a synergistic combination of (rac)-tramadol·HCl and celecoxib or a pharmaceutically acceptable salt or hydrate thereof wherein the molecular ratio of the (rac)-tramadol·HCl to the celecoxib is a molar ratio of from about 1:1 to about 1:5 or from about 1:1 to about 5:1.

2. A pharmaceutical composition according to claim 1 wherein the celecoxib is in neutral form.

3. A method for the treatment of pain comprising administering to a subject in need thereof a therapeutically effective amount of at least one pharmaceutical composition according to claim 1.

4. A method according to claim 3 wherein said pain is selected from acute pain, chronic pain, neuropathic pain, nociceptive pain, mild and severe to moderate pain, hyperalgesia, pain related to central sensitization, allodynia or cancer pain, diabetic neuropathy, diabetic peripheral neuropathy, osteoarthritis, fibromyalgia, rheumatoid arthritis, ankylosing spondylitis, frozen shoulder and sciatica.

* * * * *

(12) EX PARTE REEXAMINATION CERTIFICATE (200th)
Ex Parte Reexamination Ordered under 35 U.S.C. 257

United States Patent
Portillo Salido et al.

(10) Number: US 8,569,271 C1
(45) Certificate Issued: Nov. 12, 2021

(54) COMPOSITIONS COMPRISING TRAMADOL AND CELECOXIB IN THE TREATMENT OF PAIN

(75) Inventors: Enrique Portillo Salido, Barcelona (ES); Sebastia Videla Ces, Barcelona (ES)

(73) Assignee: ESTEVE PHARMACEUTICALS, S.A., Barcelona (ES)

Supplemental Examination Request:
No. 96/000,308, Dec. 19, 2019

Reexamination Certificate for:
Patent No.: 8,569,271
Issued: Oct. 29, 2013
Appl. No.: 13/394,995
PCT Filed: Oct. 15, 2010
PCT No.: PCT/EP2010/006317
§ 371 (c)(1),
(2), (4) Date: Mar. 8, 2012
PCT Pub. No.: WO2011/045075
PCT Pub. Date: Apr. 21, 2011

(30) Foreign Application Priority Data

Oct. 16, 2009 (EP) .................. 09384004

(51) Int. Cl.
*A61K 31/63* (2006.01)
*A61K 31/13* (2006.01)
*A61K 31/635* (2006.01)
*A61K 31/135* (2006.01)
*A61K 31/137* (2006.01)
*A61K 31/415* (2006.01)
*A61K 45/06* (2006.01)

(52) U.S. Cl.
CPC .......... *A61K 31/635* (2013.01); *A61K 31/135* (2013.01); *A61K 31/137* (2013.01); *A61K 31/415* (2013.01); *A61K 45/06* (2013.01)

(58) Field of Classification Search
None
See application file for complete search history.

(56) References Cited

To view the complete listing of prior art documents cited during the supplemental examination proceeding and the resulting reexamination proceeding for Control Number 96/000,308, please refer to the USPTO's public Patent Application Information Retrieval (PAIR) system under the Display References tab.

*Primary Examiner* — Bruce R Campell

(57) ABSTRACT

The present invention relates to pharmaceutical compositions comprising tramadol and celecoxib and their uses as medicaments or analgesics, more particularly for the treatment of severe to moderate pain with an inflammation component.

---

At the time of issuance and publication of this certificate, the patent remains subject to pending reissue application number 17/336,491 filed Jun. 2, 2021. The claim content of the patent may be subsequently revised if a reissue patent is issued from the reissue application.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-4 are cancelled.

* * * * *